United States Patent [19]

Elledge et al.

[11] Patent Number: 5,095,925

[45] Date of Patent: Mar. 17, 1992

[54] ASEPTIC CLEANING APPARATUS

[76] Inventors: David M. Elledge, 2320 N. Ralph, Tucson, Ariz. 85712; Dwain W. Smith, 3088 W. Monmouth, Tucson, Ariz. 85741

[21] Appl. No.: 322,293

[22] Filed: Mar. 13, 1989

[51] Int. Cl.$^5$ .............................................. B08B 3/12
[52] U.S. Cl. ..................... 134/61; 134/104.1; 134/184; 134/200; 134/172; 312/1
[58] Field of Search ............. 312/1; 134/61, 84, 104.1, 134/107, 200, 172, 184, 109; 51/8; 220/420

[56] References Cited

U.S. PATENT DOCUMENTS

| | | | |
|---|---|---|---|
| 2,576,008 | 11/1951 | Gladfelter et al. | 51/8 |
| 3,372,704 | 3/1968 | Ashworth | 134/109 |
| 3,410,619 | 11/1968 | Delnay et al. | 312/1 |
| 3,415,582 | 12/1968 | Trexler | 312/1 |
| 3,501,213 | 3/1970 | Trexler | 312/1 |
| 3,547,505 | 12/1970 | Ott et al. | 312/1 |
| 3,593,729 | 7/1971 | Goldware | 134/109 X |
| 3,746,020 | 7/1973 | Pekosin | 134/184 X |
| 4,059,903 | 11/1977 | Peit et al. | 32/40 |
| 4,111,753 | 9/1978 | Folsom et al. | 195/126 |
| 4,473,529 | 9/1984 | Boccon et al. | 376/314 |
| 4,865,061 | 9/1989 | Fowler et al. | 134/172 X |
| 4,886,081 | 12/1989 | Blaul | 134/200 |
| 4,886,082 | 12/1989 | Kato et al. | 134/184 |

*Primary Examiner*—Frankie L. Stinson
*Attorney, Agent, or Firm*—Victor Flores

[57] ABSTRACT

This invention discloses a fluid sterile system for use in the medical and dental industries for the removal and cleaning of gross tissue forms from biological articles and a method of preparing the biological articles for transplant and corrective surgeries and in the electronic and aerospace industries, the present invention discloses a portable, fluid cleaning system that clean articles such as fixtures, aerospace electronic and other equipment, microelectronic chips and electronic printed circuit boards for reducing the contamination level of such articles measured in parts per million (ppm). The aseptic system includes an enclosed high pressure sterile jet cleaning apparatus member for use in a first stage cleaning of particulates from an article used in a particular industry and a sterile ultrasonic bath apparatus member for use in a second stage cleaning of particulates from the same article.

17 Claims, 6 Drawing Sheets

ASEPTIC CLEANING APPARATUS

FIELD OF THE INVENTION

The present invention pertains to systems used in medical and electronic industry having a sensitivity for regulating contaminants that will be in contact with articles such as osteopathic articles, or microelectronic chip articles, respectively in each industry. More particularly, the present invention is related to portable, fluid sterile systems used in the medical and dental industries for the removal and cleaning of gross tissue forms from biological articles and preparing the biological articles for transplant and corrective surgeries and in the electronic and aerospace industries, the present invention relates to portable, fluid cleaning systems that clean articles such as fixtures, aerospace electronic and other equipment, microelectronic chips and electronic printed circuit boards for reducing the contamination level of such articles measured in parts per million (ppm).

BACKGROUND OF THE PRIOR ART

Medical

One hundred to two hundred thousand tissue transplants are annually performed in the United States. Thus, it is in the realm of preparing these samples that the present invention will find tremendous medical applications. The single most variable factor with respect to allographic transplantation is the preparation of such bone and tissue segments. Procedure and protocol of the sum 400 tissue banks in North America is quite varied and has resulted in a void of technology with developed process at a cost effective level. There is no known industry standard specifying levels of cleanliness for cleaning and preparing bone segments. The problems associated with this lack of standards interpret to poor process control, inadequate removal of tissue from the parent surface and to a large extent lack of sterility during the cleaning process.

The upper portion of FIG. 12 shows the known process, generally designated 400, relating to allotropic tissues, as beginning by removal of a segment from a donor 401, generally a cadaveric donor within 24 hours after cessation of life. Upon removal of large segments, i.e. the pelvis, the long bones of the legs, and intact joints, then the outer fleshy components and connective tissue, ligamentary tissues, are removed from the bone, via osteotomies 402 that are mechanical hand held instruments adapted for cleaning and preparing the bone tissues and for use in close contact with the bone segment surface for removal of fleshy connective tissues from the bone. The removal of the large segments may or not be done in a sterile environment, i.e. a hospital morgue, a side room at less than operating room sterility. The segments are then subjected to a low pressure, often nonsterile fluid 402 such as tap water at 35 to 40 p.s.i. The most modern method of cleaning bone segments still use the osteotomies but may use a low delivery non-sterile fluid but use clean room environment to do the cleaning of the bone segment. The osteotome cleaned bone segments are not considered sterile and are thus further processed with a secondary sterilant, generally using liquid and gaseous ethylene oxide 403 or gamma irradiation 404. Alternatively, the segment may be preserved using lyophilization techniques 405. The lyophilization does not sterilize but rather removes water to prevent further growth of any virus. The gamma irradiation 404 and ethylene oxide 403 processes, while providing a sterile segment, neither will get the segment any cleaner. Both processes are known to have deleterious effects at the oncogenic and mutagenic potential levels. The segments sterilized using etheyene oxide (eto) may be stored, in a suitable storage facility 406 for six months then the segments must be reintroduced to the eto sterilization process. The resterilization may only be done a maximum of three times, then the segment must be discarded. Obviously, a costly situation exists in addition to the mutagenic and oncogenic risks.

Electronic and Aerospace Industries

The methods used for cleaning articles used in these industries are more defined and better controlled as is evident by clean room apparatuses taught by the prior art.

U.S. Pat. No. 4,111,753 to Folson et al. teaches a controlled atmosphere system comprising an incubation apparatus. Of interest is the teaching of the transparent, flexible hood that allows specimens to be observed.

U.S. Pat. No. 4,473,529 to Baccon-Gibod teaches a device for collecting radioactive purge liquids and gases.

U.S. Pat. No. 2,576,008 to Gladfelter et al. teaches a wet blasting machine wherein of interest is the teaching of a housing provided with a vision window, arm holes terminating in sleeves.

U.S. Pat. No. 3,415,582 to Trexter teaches a tetrahedron isolator including an enclosed housing hermetically sealed from the surrounding atmosphere. The isolator includes a fluid inlet and outlet to control the atmosphere within the housing by supplying sterile fluids under pressure to the interior of the isolator. Glove ports are also provided.

U.S. Pat. No. 3,501,213 to Trexter teaches a locker structure enabling a person to leave an isolator structure.

U.S. Pat. No. 4,059,903 to Piet et al. teaches a controlled atmosphere work enclosure wherein of interest is the teaching of an enclosure provided with a filtering means, a viewing panel and glove port.

SUMMARY OF THE INVENTION

The present invention is an aseptic system apparatus and method for use in medical, microelectronic and aerospace industries, the aseptic system apparatus comprises a high pressure sterile jet cleaning apparatus member for use in a first stage cleaning of particulate from an article used in said industries and a sterile ultrasonic bath apparatus member for use in a second stage cleaning of particulate from said article used in said industries.

The high pressure sterile jet cleaning apparatus member is designed to comprise, a fluid source means, a sterile fluid path means for circulating a first fluid during an initial sterile preparation of said jet cleaning apparatus member and for delivering a second fluid from said fluid source means to said article being cleaned, said fluid source means being mechanically coupled to said sterile fluid path means, an enclosure means for providing a sterile and controlled environment for cleaning said article, said enclosure means being mechanically coupled to said fluid path means, a fluid jet means for jet cleaning said article, said fluid jet means being mechanically coupled to a terminating end of said fluid path means within said enclosure means, and a sterile wall and floor liner means, said liner means being fitted within said enclosure means and being used for filtering particulate, for abrading said article being cleaned and for damping said second fluid being propelled against side walls of said enclosure means, said damping controlling visibility into said enclosure means.

The sterile ultrasonic bath apparatus member comprises at least one ultrasonic cleaning tank for submersion and ultrasonically cleaning said article, a first liquid contained in said tank for use during an initial sterile preparation of said ultrasonic bath apparatus member, a second liquid contained in said tank after said initial sterile preparation for use during said second stage cleaning, said second stage cleaning being ultrasonic cleaning, a transducer means for generating ultrasonic energy within said second liquid for facilitating said ultrasonic cleaning, said transducer means having an operating frequency that enables excision of said second liquid to cavitation without significantly eroding said article being cleaned, a heat exchanger means for maintaining said second liquid and said article at a specified working temperature range by removing thermal energy in said second liquid, said heat exchanger means being hydraulically coupled to said at least one ultrasonic cleaning tank, and a pump, such as a variable flow rate peristaltic pump, said pump being hydraulically coupled to said heat exchanger means and to said at least one ultrasonic cleaning tank to form a closed hydraulic loop system, said pump being provided with a control circuit for cycling said bath fluid at a variable flow rate to maintain said second liquid within a specified working temperature range.

The present invention has particular utilization in the medical field where the article being cleaned is an osteopathic segment for allotropic, autotropic, zenotropic and artificial transplants.

It is an object of the present invention to provide a system for the sterile preparation of articles used in medical and electronic industry having a sensitivity for regulating contaminants that will be in contact with articles such as osteopathic articles, or microelectronic chip articles, respectively in each industry.

It is a particular object of this invention to provide a system for the sterile preparation of transplantable tissue. The needs filled by said system on a broad scale will be a unification of procedure and protocol for allographic tissue preparation, consistent performance and results of tissue processing centers, reduced detrimental effects of toxic chemicals and radiation now used by ¼ of bone banking community, dramatic increase in the quality of allographic materials produced, decreased post-operative infection and transmission of disease, negation of local environmental factors such as toxic and pollutants found in city waters supplies that many hospitals use in North America and quicker functional incorporation of transplanted allografts.

It is another object of the present invention to provide a system for the sterile preparation of transplantable tissue that will avoid the application of secondary sterilants that produce deleterious effects in the host site and body.

It is yet another object of the present invention to provide a system for the sterile preparation of transplantable tissue that will increase the shelf life, product quality, component integrity, derive consistent and uniform results of prepared tissue and reduce the preparatory overhead expense.

Therefore, to the accomplishments of the foregoing objects, the invention consists of the foregoing features hereinafter fully described and particularly pointed out in the claims, the accompanying drawing and following disclosure describing in detail the invention, such drawing and disclosure illustrating, however, but one of the various ways in which the invention may be practiced.

PREFERRED EMBODIMENT OF THE INVENTION

Figures 1, 2:
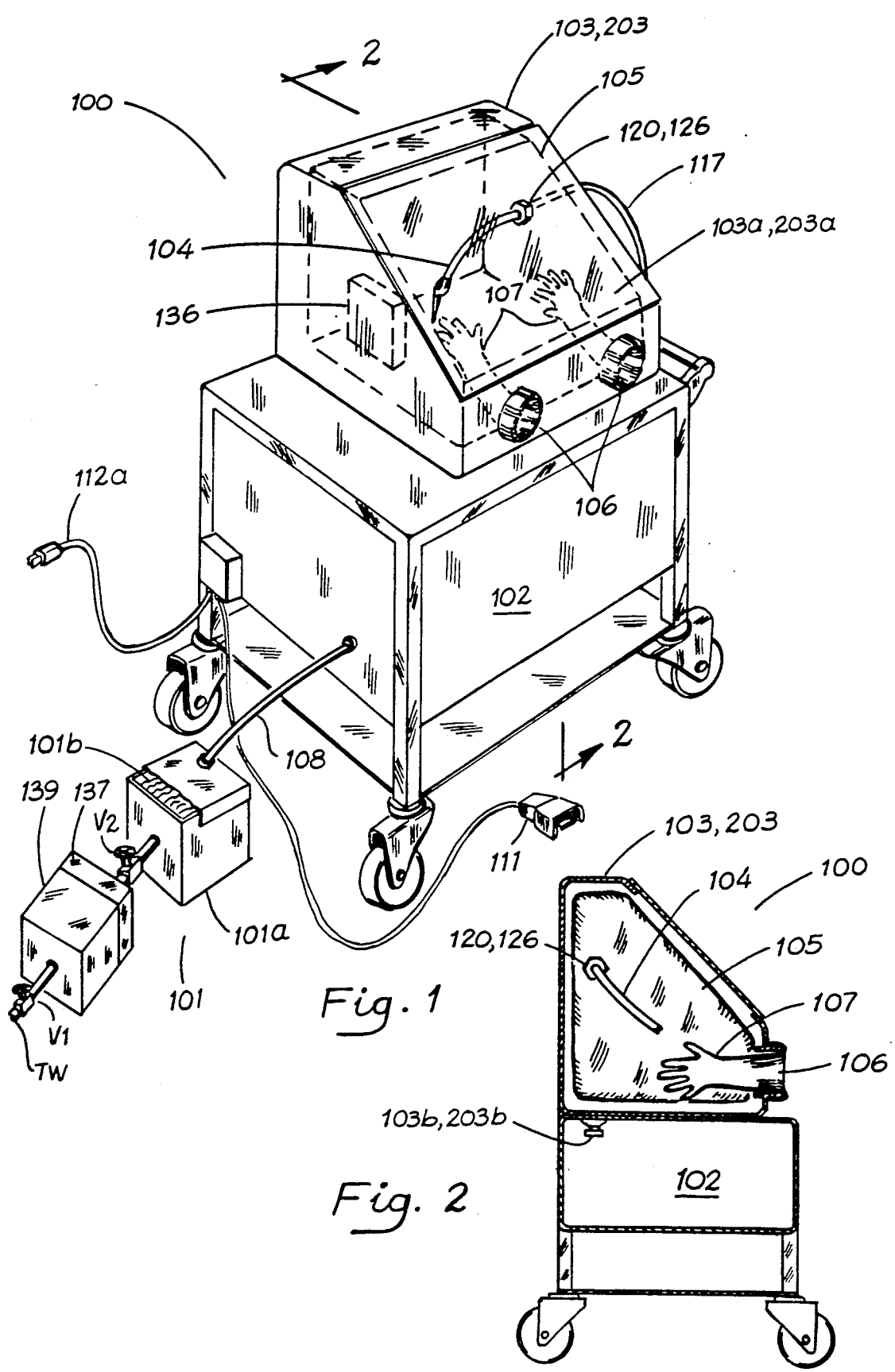
FIG. 1 is a perspective of the high pressure sterile jet cleaning apparatus member of the present invention.
FIG. 2 is a sectional side view taken along the line 2—2 of FIG. 1 of the jet enclosure showing the glove ports.
Figure 3:
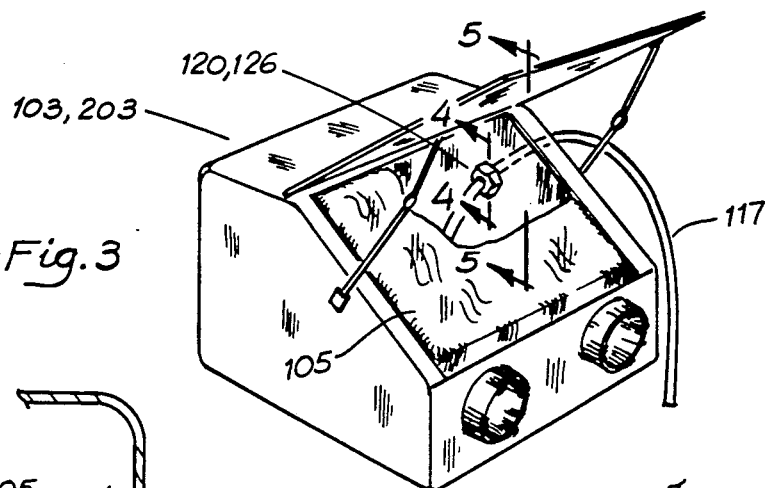
FIG. 3 is a perspective view of the jet enclosure showing the wall liner and the hinged transparent lid and fluid inlet interface.
Figure 7:
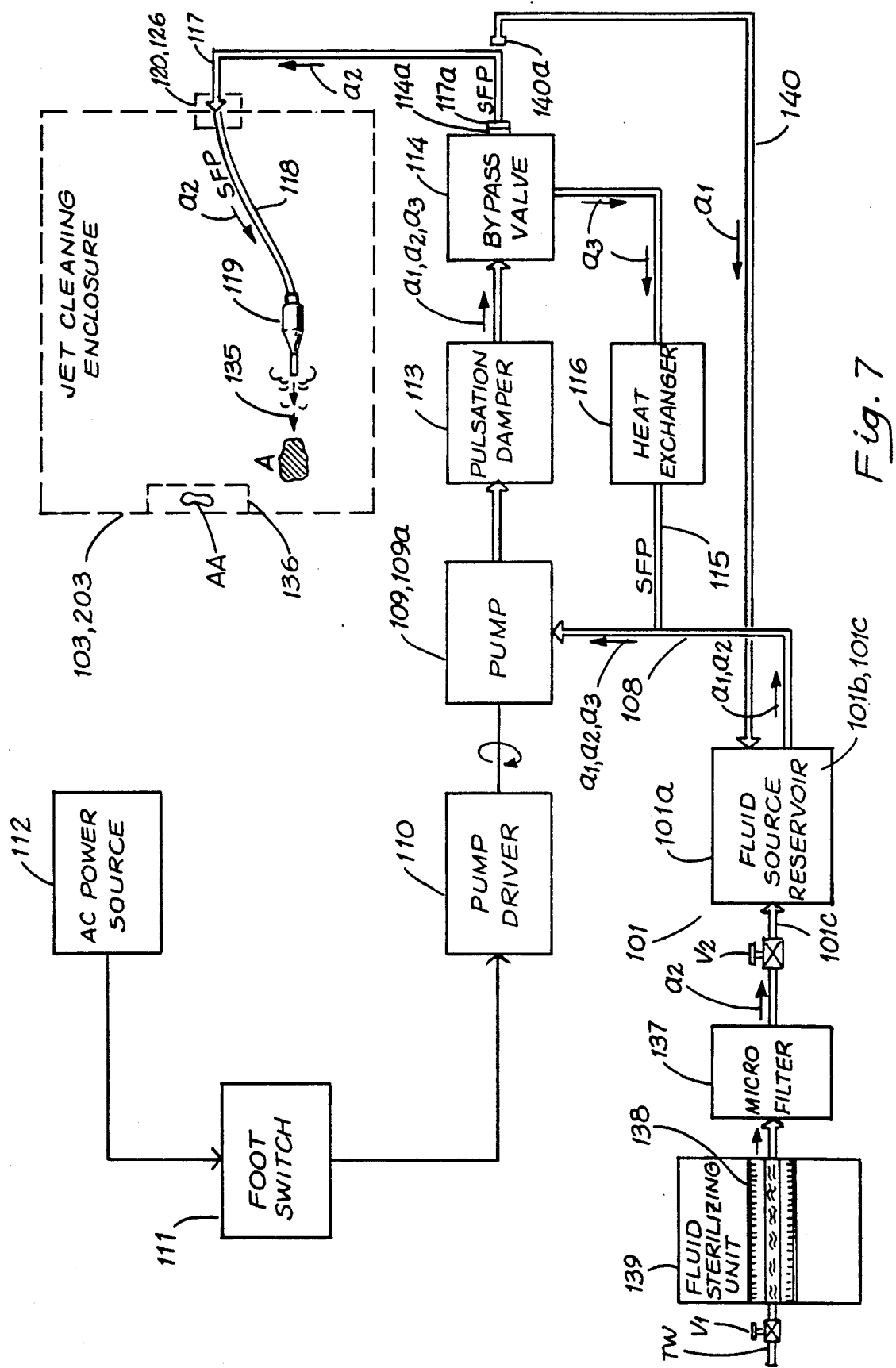
FIG. 7 is a schematic representation of the high pressure sterile jet cleaning apparatus member of the present invention.
Figure 8:
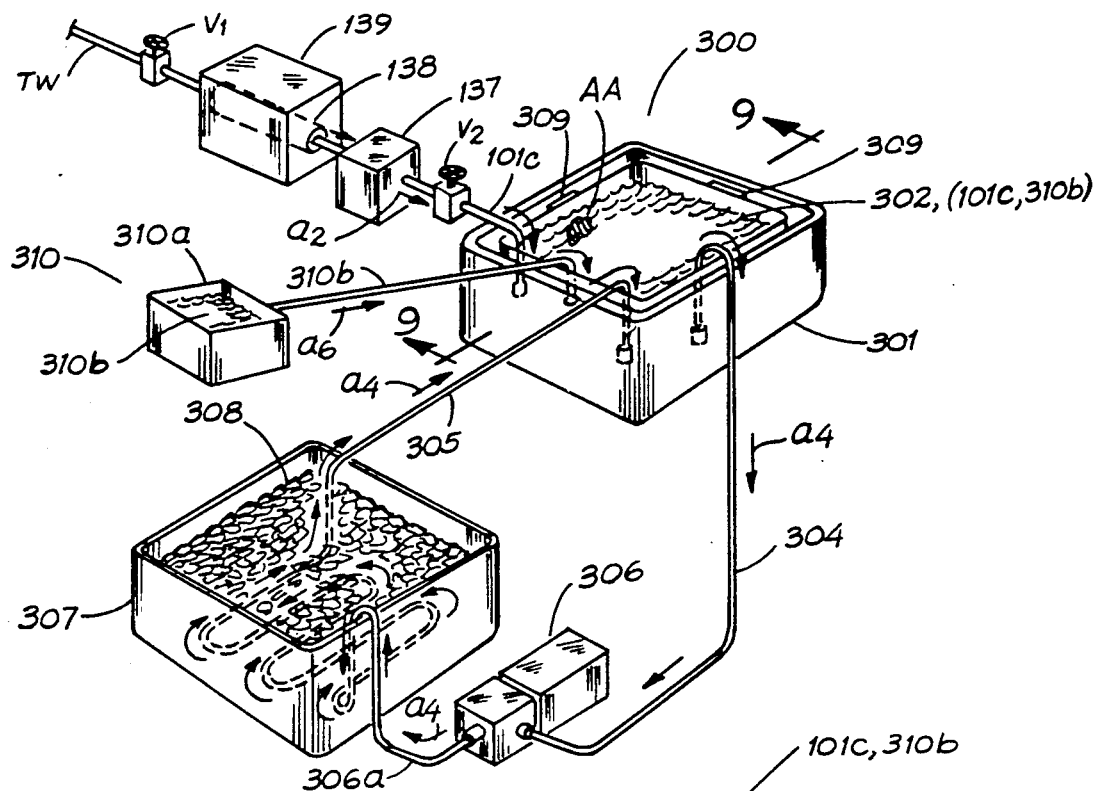
FIG. 8 is a schematic representation of the sterile ultrasonic bath apparatus member of the present invention.

Referring now to the drawings and more particularly to FIGS. 1, 7 and 8, the high pressure sterile jet cleaning apparatus member 100 and the sterile ultrasonic bath apparatus member 300 are shown.

High pressure sterile jet cleaning apparatus member 100 is designed to comprise, a fluid source means 101, a power unit 102 and a jet enclosure means 103, 203 (enclosure means 203 being a stainless steel version while enclosure means 103 is a disposable enclosure version). Fluid source means 101 includes a tap water source TW, a first shut-off valve v1, coupled to a fluid sterilizing unit 139 provided with a photon energy means 138 and micro filter 137, coupled to a second shut-off valve v2 for delivering, as shown by flow arrow a2 a second sterile fluid 101c to fluid source reservoir 101a that can also contain a sterilant first fluid 101b. The sterile fluid source 101 is coupled to power unit 102 by way of pump input hose 108.

FIGS. 1 and 7 shows power unit 102 being electrically coupled to a power source 112 by way of power cable 112a and controlled by a foot switch 111. The power unit 102 forms a sterile fluid path means (sfp) for circulating, as shown by flow arrow a1, a first fluid 102 during an initial sterile preparation of said jet cleaning apparatus member 100 and for delivering a second fluid 101c from said fluid source means 101 to an article A being cleaned in a first stage cleaning operation 501 (see FIG. 12). The power unit 102 comprises components designed for pressures greater than 300 p.s.i. and being highly chemical resistive to fluids such as said sterilant first fluid 101b. The components of power unit 102 comprises a pump driver 110, pump means 109, pulsation damper means 113, bypass valve means 114 and heat exchanger 116. Pump driver 110 being electrically coupled to manually operated switch 111, pump 109 being provided with seals, O-rings, and cups (generally designated az) made from a highly chemical resistive material, such as VITON and TEFLON and adapted to provide an injection port (not shown) for injecting secondary fluids and substances as needed, pump 109 is used for pumping first and second fluids 101b and 101c from said fluid source reservoir 101a, pump means 109 being mechanically connected to pump driver 110 and to fluid source reservoir 101a, pulsation damper means 113 damping impulses caused by high pressure demands on said sterile fluid path, damper means 113 being mechanically coupled to pump means 109, bypass valve means 114 directing first and second fluids 101b and 101c to a fluid jet means 104, provided with nozzle 119, via quick disconnect couplings 114a, 117a and enclosure inlet interface 120, 126 (interface 126 being the used for the stainless steel enclosure version 203) and to heat exchanger means 116, bypass valve means 114 being mechanically coupled to pulsation damper means 113, heat exchanger means 116 maintaining, as shown by flow arrow a3, first and second fluids 101b and 101c at a suitable temperature for human contact, heat exchanger means 116 being mechanically coupled at an input end to said bypass valve 114 and at an output end to an input end of said pump means 109 via a feedback hose 115. A circulating return line 140 is provided for coupling to bypass valve 114 via quick disconnect coupling 140a and forming a closed loop pumping cycle during said initial sterile preparation.

FIGS. 1, 2, 3 and 7 shows enclosure means 103, 203, which means provides a sterile and controlled environment for cleaning article, designated A, Enclosure means 103 is functionally the same as enclosure means 203, but differs structurally in that means 103 is a disposable polycarbonate unit while means 203 is a stainless steel reusable version that may be resterilized after each use. Means 103 may be attractive from a risk management and cost containment perspective. Enclosure means 103, 203 being mechanically coupled to power unit 102 via hose 117 to inlet interface 120, 126 (enclosure 126 being the inlet interface for stainless steel enclosure version 203). Interface 120, 126 couples fluid jet means 104 to supply high pressure fluid 135 (fluid 135 being second fluid 101c) for jet cleaning article A. Fluid jet means 104 being mechanically coupled from nozzle 119 via hose 118 to interface 120, 126. Enclosure means 103, 203 is provided with sterile wall and floor liner means 105, liner means 105 being fitted within enclosure means 103, 203 and being used for filtering particulates, for abrading article A being cleaned and for damping high pressure fluid 135 (second fluid 101c) being propelled against side walls of enclosure means 103, 203, the damping of the high pressure fluid 135 controlling visibility into enclosure means 103, 203. Enclosure means 103, 203 further comprises at least one pair of glove ports 106 for allowing access by a technician using gloves 107 to operate fluid jet means 104 and to manipulate and clean article A, a transparent lid 103a, 203a provided on a top portion of enclosure means 103, 203 for viewing of article A being cleaned, at least one storage vesicle 136 located on a wall of enclosure means 103, 203 for storing cleaned articles AA and drain port 103b, 203b located on a bottom surface of enclosure means 103, 203, drain port 103b, 203b being covered by wall and floor liner means 105.

Figure 5:
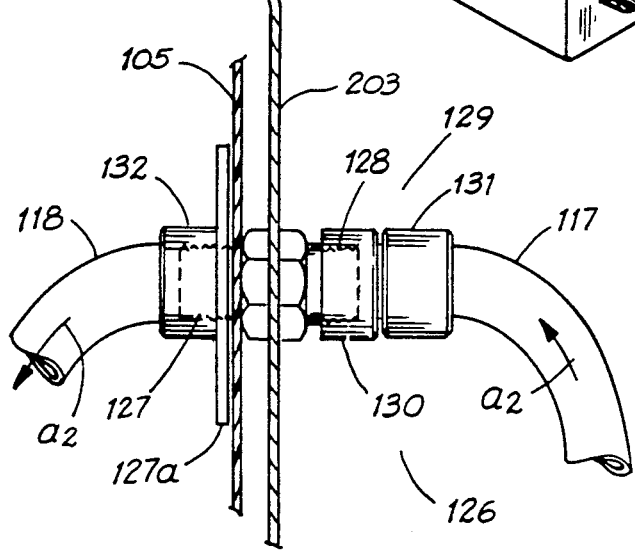
FIG. 5 is a sectional view of the stainless steel inlet interface taken along the line 5—5 of FIG. 3.
Figure 4:
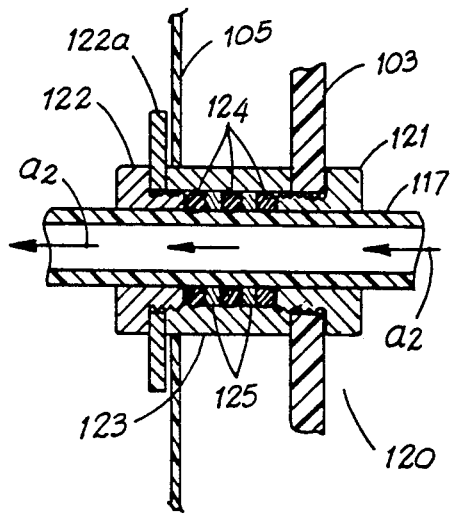
FIG. 4 is a sectional view of the polycarbonate inlet interface taken along the line 4—4 of FIG. 3.
Figure 6:
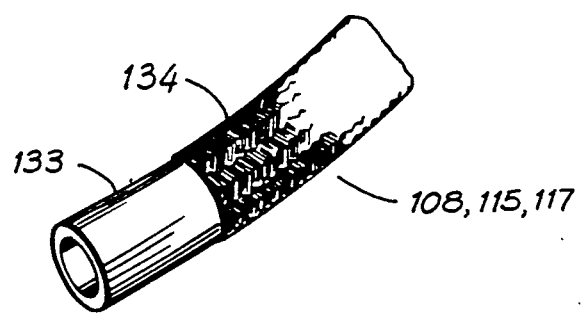
FIG. 6 is a partial perspective view of the sheathed, highly chemically resistive hose material used in the fluid path.

FIGS. 4, 5 and 6 show enlarged views of enclosure inlet interfaces 120, 126 and of hoses 108, 115 and 117. Interface 120 illustrates hose 117 being coupled through enclosure 103 and wall liner 105 using threaded sleeve 123 positioned therebetween and circumferentially sealed with O-rings 124 and O-ring spacers 125 and being sealed on the interior by annular screw 122 and washer 122a and sealed on the exterior by annular screw 121. For stainless steel enclosure 203, the interface is by a conventional quick disconnect interface between the liner 105 and a wall of enclosure 203 including nipples 127 and 128, washer 127a. Hose 117 being provided with fitting 131 for mating with fitting 130 to form coupled joint 129. Hose 118 is provided with threaded fitting 132 for coupling to nipple 127. Hoses 108, 115 and 117 must be highly durable and capable of resisting sterilant chemical and high pressure pulsating action. FIG. 6 shows hoses 108, 115 and 118 being constructed of a braided sheathing 134 and inner tubing 133 from a material such as TEFLON.

Figure 9:
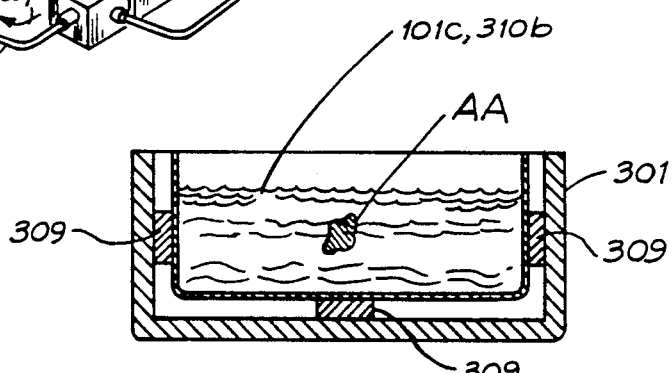
FIG. 9 is a sectional view of the ultrasonic cleaning tank member taken along the line 9—9 of FIG. 8 showing the segment AA submersed in a second liquid mixture.
Figure 12:
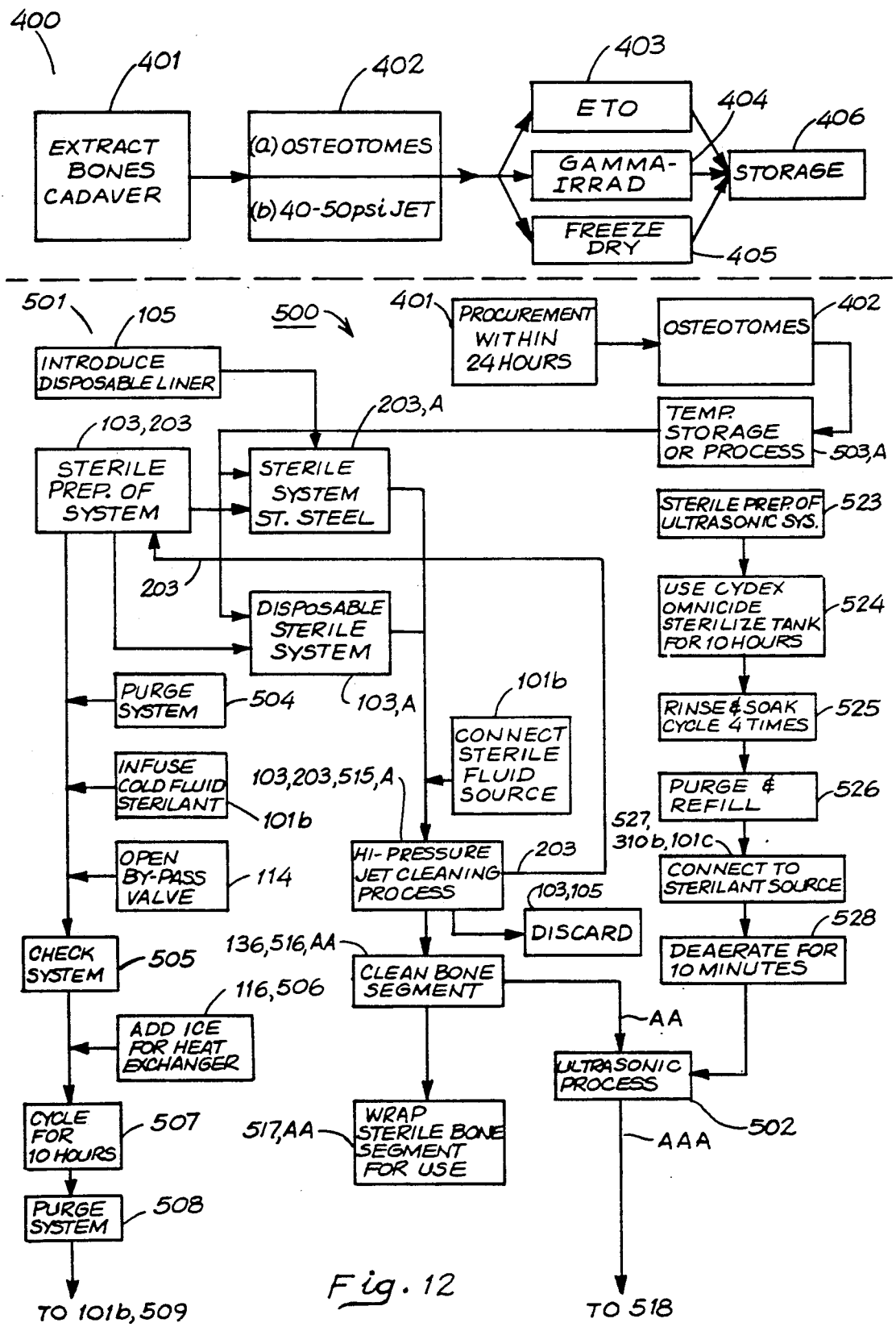
FIG. 12 is a block diagram representation of the prior art method of cleaning a bone segment and a block flow diagram representation of the preparation and utilization of the system apparatus of the present invention.

FIG. 8 shows sterile ultrasonic bath apparatus member 300 comprising at least one ultrasonic cleaning tank 301 for submersion and ultrasonically cleaning article AA per process 502 (see FIG. 12). First liquid 302, containable in tank 301, is used during an initial sterile preparation of ultrasonic bath apparatus member 300, a second liquid (101c, 310b), also containable in tank 301, is used after the initial sterile preparation for the second stage cleaning of article A, the second stage cleaning being ultrasonic cleaning process 502. First liquid 302 is a sterilant substance, such as CYDEX or OMNICIDE, while second liquid (101c, 310b) is a mixture of de-ionized water 101c and a surfactant substance 310b. The de-ionized water is processed similar to fluid source 101 while surfactant 310b is obtained, as shown by flow arrow a6, from a secondary substance pumping system 310 having a holding tank 310a and interconnecting tubing 310b. Tank 301 is provided with a transducer means 309 for generating ultrasonic energy within second liquid (101c, 310b) for facilitating ultrasonic cleaning, see also FIG. 9. Transducer means 309 having an operating frequency (typically greater than 20,000 Hz) that enables excition of second liquid (101c, 310b) to cavitation without significantly eroding article AA being cleaned. System 300 is provided with pump 306 and heat exchanger means 307 for circulating and maintaining second liquid (101c, 310B) and article AA at a specified working temperature range by removing thermal energy in second liquid (101c, 310b) using a cooling medium 308. Pump 306 being hydraulically coupled to heat exchanger means 307 and to ultrasonic cleaning tank 301 to form a closed hydraulic loop system, shown by flow arrow a4. Heat exchanger means 307 being hydraulically coupled to cleaning tank 301 via tubing 306a, which is connected to pump 306, which is connected to tubing 304, which is submerged in tank 301, which receives cooled liquid from tubing 305 which is connected to heat exchanger 307. Tubing 304, 305 and 306a being made from a highly chemical resistive material, such as TYGON. Pump 306 is preferably a variable flow rate peristatlic pump. Pump 306 being provided with a control circuit (not shown) for cycling second liquid (101c, 310b) at a variable flow rate to maintain within a specified working temperature range (typically within 27 and 33 degrees Celsius).

OPERATION OF THE PREFERRED EMBODIMENT

Figure 13:
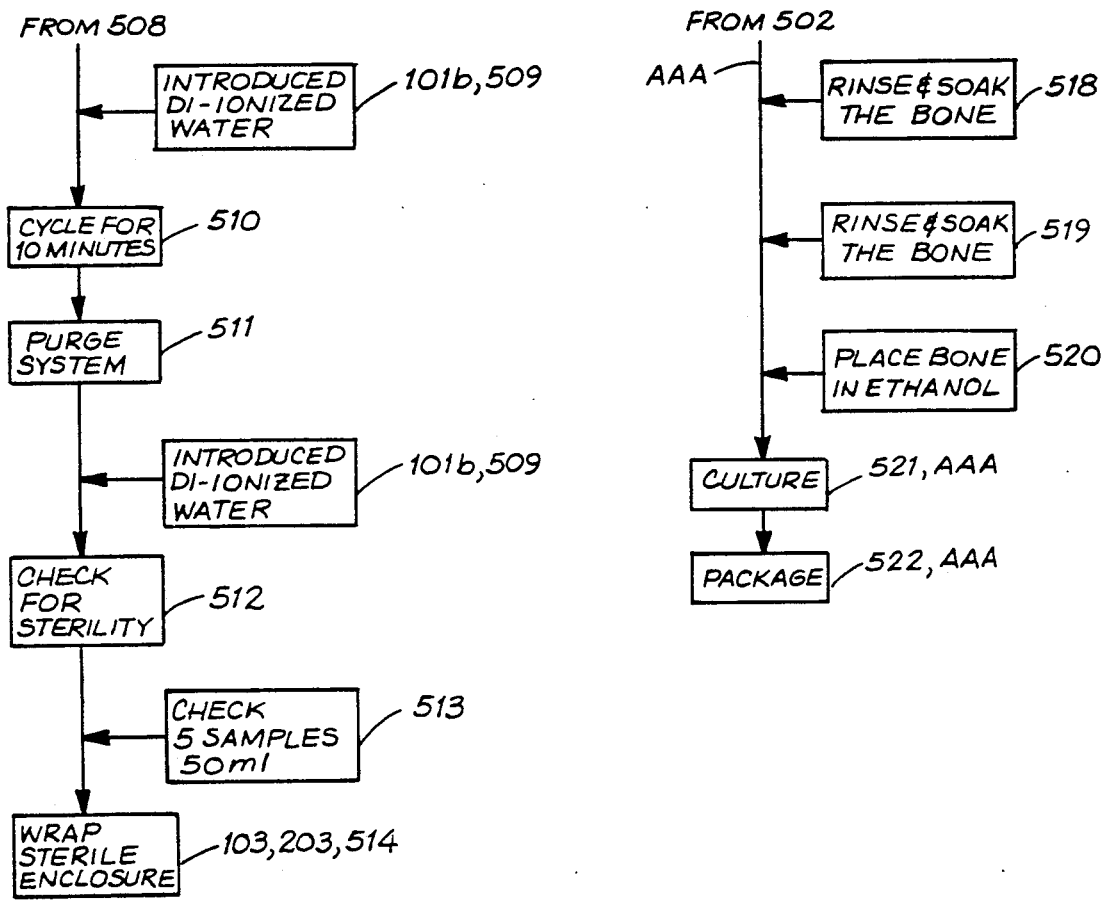
FIG. 13 is a continuation of FIG. 12.

Referring now to FIGS. 12 and 13 the high pressure sterile jet cleaning process 501 and the sterile ultrasonic bath cleaning process 502 are shown in a two stage cleaning process, generally designated 500. Under the present invention, bone segments are extracted from a doner 401 and are preliminarily cleaned using osteotomies 402 and stored as transplantable tissue article A in a storage facility 503. The present system requires an initial sterilization preparation of system apparatus 100 before being used. The preparation may apply to disposable enclosure 103 or to the stainless steel enclosure 203. The flow diagram shows enclosure 203 as being returned for sterile preparation after a use cycle. The initial preparation comprises a purging step 504, introducing sterilant 101b, opening by-pass valve 114, a checking step 505, adding ice step 506 to heat exchanger 116, a 10 hour cycle step 507, a second purging step 508, an adding step 509 for introducing of de-ionized water 101b, a second cycling step 510, a final purging step 511, repeating step 509, a checking for sterility steps 512, 513 and a wrapping sterile enclosure step 514. Either enclosure 103 or 203 may be used for the task at hand. If enclosure 203 is being used, wall liner 105, commercially available as SCOTCHBRITE, is added after sterile preparation. The process may begin by connecting the sterile fluid source 101b to begin a hi-pressure cleaning step 515 to produce a cleaned segment AA for a interim storage step 516 or an end use wrapping step 517. The particular transplanting requirements determines whether to use the cleaned segment AA or to continue with the process. It should be understood that enclosure 103 and liner 105 are discarded after use.

Figure 10:
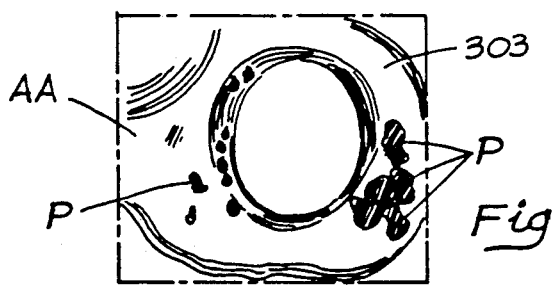
FIG. 10 is an enlarged cutaway view of a segment AA illustrating particulates that remain after a first stage of cleaning.
Figure 11:
FIG. 11 is an enlarged view of a segment AAA illustrating the particulates removed after being ultrasonically cleaned.
Figure 9A:
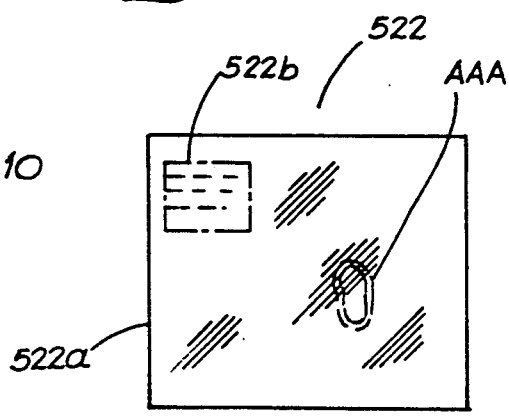
FIG. 9a is a view of a labeled packaged segment AAA after being ultrasonically cleaned.

If the requirements are to continue, then sterile ultrasonic bath cleaning process 502 follows. The ultrasonic system 300 also requires an initial sterile preparation step 523. The preparation 523 comprises circulating step 524 using a sterilant, rinsing and soaking step 525, purging and refilling step 526, adding the sterile second liquid mixture (101c, 310b) and a deaerateing step 528. After preparation of apparatus 300, article AA is submerged in the second liquid 101c, 310b) and ultrasonically cleaned, rinsed and soaked per steps 518 and 519 and reintroduced to the ultrasonic process 502 if necessary. Once cleaned, the segment A then further processed in an ultrasonic chemical dehydration step 520 to accelerate drying of the segments. The step 520 may included the use of ethanol in deionized water, the exact concentration levels of deionized water and ethanol may be varied to produce different dehydration times. After dehydration, the segment AAA is cultured per step 521 and the packaged and readied for use or storage per step 522. FIG. 9a shows packaging step 522 including the use of package 522a labeling 522b. FIGS. 10 and 11 illustrate the improvements in subjecting a bone segment AA having particulates P on surface 303 to the ultrasonic process 502 to produce a cleaner segment AAA.

Therefore, while the present invention has been shown and described herein in what is believed to be the most practical and preferred embodiment, it is recognized that departures can be made therefrom within the scope of the invention, which is therefore not to be limited to the details disclosed herein but is to be accorded the full scope of the claims so as to embrace any and all equivalent apparatus.

We claim:

1. An aseptic system apparatus for use in medical, microelectronic and aerospace industries, said aseptic system apparatus comprising:
   (a) a high pressure sterile jet cleaning apparatus member for use in a first stage cleaning of particulates from an article used in said industries; and
   (b) a sterile ultrasonic bath apparatus member for use in a second stage cleaning of particulates from said article used in said industries, said sterile ultrasonic bath apparatus member comprising:
   (i) at least one ultrasonic cleaning tank for submersion and ultrasonically cleaning said article,
   (ii) a first liquid contained in said tank for use during an initial sterile preparation of said ultrasonic bath apparatus member, and
   (iii) a second liquid contained in said tank after said initial sterile preparation for use during said second stage cleaning, said second stage cleaning being ultrasonic cleaning.

2. An aseptic system apparatus for use in medical, microelectronic and aerospace industries as recited in claim 1 wherein said sterile ultrasonic bath apparatus member further comprises:
   (iv) a transducer means for generating ultrasonic energy within said second liquid for facilitating said ultrasonic cleaning, said transducer means having an operating frequency that enables excition of said second liquid to cavitation without significantly eroding said article being cleaned,
   (v) a heat exchanger means for maintaining said second liquid and said article at a specified working temperature range by removing thermal energy in said second liquid, said heat exchanger means being hydraulically coupled to said at least one ultrasonic cleaning tank, and
   (vi) a pump means, said pump means being hydraulically coupled to said heat exchanger means and to said at least one ultrasonic cleaning tank to form a closed hydraulic loop system, said pump means being used for cycling said bath fluid and maintaining said second liquid within said specified working temperature range.

3. An aseptic system apparatus for use in medical, microelectronic and aerospace industries as recited in claim 1, wherein said second liquid having a substantially reduced surface tension in comparison with deionized water and providing a substantially increased ultrasonic cleaning action.

4. An aseptic system apparatus for use in medical microelectronic and aerospace industries as recited in claim 1, wherein said second liquid contains a surfactant for reducing said surface tension.

5. An aseptic system apparatus for use in medical, microelectronic and aerospace industries, said aseptic system apparatus comprising:
(a) a high pressure sterile jet cleaning apparatus member for use in a first stage cleaning of particulates from an article used in said industries; and
(b) a sterile ultrasonic bath apparatus member for use in a second stage cleaning of particulates from said article used in said industries, said sterile ultrasonic bath apparatus member comprises,
  (i) at least one ultrasonic cleaning tank for submersing and ultrasonically cleaning said article,
  (ii) a first liquid contained in said tank for use during an initial sterile preparation of said ultrasonic bath apparatus member,
  (iii) a second liquid contained in said tank after said initial sterile preparation for use during said second stage cleaning, said second stage cleaning being ultrasonic cleaning,
  (iv) a transducer means for generating ultrasonic energy within said second liquid for facilitating said ultrasonic cleaning, said transducer means having an operating frequency that enables excition of said second liquid to cavitation without significantly eroding said article being cleaned,
  (v) a heat exchanger means for maintaining said second liquid and said article at a specified working temperature range by removing thermal energy in said second liquid, said heat exchanger means being hydraulically coupled to said at least one ultrasonic cleaning tank, and
  (vi) a variable flow rate peristaltic pump, said pump being hydraulically coupled to said heat exchanger means and to said at least one ultrasonic cleaning tank to form a closed hydraulic loop system, said pump being provided with a control circuit for cycling said bath fluid at a variable flow rate to maintain said second liquid within said specified working temperature range.

6. An aseptic system apparatus for use in medical, microelectronic and aerospace industries as recited in claim 5, wherein said high pressure sterile jet cleaning apparatus member comprises,
  (i) a fluid source means,
  (ii) a sterile fluid path means for circulating a first fluid during an initial sterile preparation of said jet cleaning apparatus member and for delivering a second fluid from said fluid source means to said article being cleaned, said fluid source means being mechanically coupled to said sterile fluid path means,
  (iii) an enclosure means for providing a sterile environment for cleaning said article, said enclosure means being mechanically coupled to said fluid path means,
  (iv) a fluid jet means for jet cleaning said article, said fluid jet means being mechanically coupled to a terminating end of said fluid path means within said enclosure means, and
  (v) a wall and floor liner means, said liner means being fitted within said enclosure means and being used for filtering particulates, for abrading said article being cleaned and for damping said second fluid being propelled against side walls of said enclosure means, said damping controlling visibility into said enclosure means.

7. An aseptic system apparatus for use in medical, microelectronic and aerospace industries, said aseptic system apparatus comprising:
(a) a high pressure sterile jet cleaning apparatus member for use in a first stage cleaning of particulates from an article used in said industries, said high pressure sterile jet cleaning apparatus member comprising,
  (i) a fluid source means,
  (ii) a sterile fluid path means for circulating a first fluid during an initial sterile preparation of said jet cleaning apparatus member and for delivering a second fluid from said fluid source means to said article being cleaned, said fluid source means being mechanically coupled to said sterile fluid path means,
  (iii) an enclosure means for providing a sterile environment for cleaning said article, said enclosure means being mechanically coupled to said fluid path means,
  (iv) a fluid jet means for jet cleaning said article, said fluid jet means being mechanically coupled to a terminating end of said fluid path means within said enclosure means, and
  (v) a wall and floor liner means, said liner means being fitted within said enclosure means and being used for filtering particulates, for scrubbing said article being cleaned and for damping said second fluid being propelled against side walls of said enclosure means, said damping controlling visibility into said enclosure means; and
(b) a sterile ultrasonic bath apparatus member for use in a second stage cleaning of particulates from said article used in said industries, said sterile ultrasonic bath apparatus member comprises,
  (i) at least one ultrasonic cleaning tank for submersing and ultrasonically cleaning said article,
  (ii) a first liquid contained in said tank for use during an initial sterile preparation of said ultrasonic bath apparatus member,
  (iii) a second liquid contained in said tank after said initial sterile preparation for use during said second stage cleaning, said second stage cleaning being ultrasonic cleaning,
  (iv) a transducer means for generating ultrasonic energy within said second liquid for facilitating said ultrasonic cleaning, said transducer means having an operating frequency that enables excition of said second liquid to cavitation without significantly eroding said article being cleaned,
  (v) a heat exchanger means for maintaining said second liquid and said article at a specified working temperature range by removing thermal energy in said second liquid, said heat exchanger means being hydraulically coupled to said at least one ultrasonic cleaning tank, and
  (vi) a variable flow rate peristaltic pump, said pump being hydraulically coupled to said heat exchanger means and to said at least one ultrasonic cleaning tank to form a closed hydraulic loop system, said pump being provided with a control circuit for cycling said bath fluid at a variable flow rate to maintain said second liquid within said specified working temperature range.

8. An aseptic system apparatus for use in medical, microelectronic and aerospace industries as recited in claim 7, wherein said second liquid having a substantially reduced surface tension in comparison with deionized water and providing a substantially increased ultrasonic cleaning action.

9. An aseptic system apparatus for use in medical, microelectronic and aerospace industries as recited in claim 8, wherein said second liquid contains a surfactant.

10. An aseptic system apparatus for use in medical, microelectronic and aerospace industries as recited in claim 9, wherein said liquid being biodegradable and compatible with an intended use of said article in said industries, said cleaning tank being volumetrically sized to allow economical purging of said bath liquid mixture after an ultrasonic cleaning cycle.

11. An aseptic system apparatus for use in medical, microelectronic and aerospace industries as recited in claim 7, wherein said fluid source comprising a container member used for containing said first fluid during said initial sterile preparation and for containing said second fluid used during said first stage cleaning of said article, said second fluid being a sterile fluid produced in a sterilizing unit comprising a photon energy means for imparting energy and eliminating residual pyrogens during production of said second fluid and a micron pyrogenic filtration means for filtering pyrogens that may be present in said produced second fluid.

12. An aseptic system apparatus for use in medical, microelectronic and aerospace industries as recited in claim 7, wherein said sterile fluid path means comprises components designed for pressures greater than 300 p.s.i. and being highly chemical resistive to fluids such as said first fluids, said first fluid being a sterilant.

13. An aseptic system apparatus for use in medical, microelectronic and aerospace industries as recited in claim 12, wherein said components comprises:
   (a) a pump driver, said pump driver being electrically coupled to a manually operated switch that is further electrically coupled to a power source;
   (b) a pump means for pumping said first and second fluids from said fluid source, said pump means being mechanically connected to said pump driver and mechanically connected to said fluid source;
   (c) a pulsation damper means for damping impulses caused by high pressure demands on said sterile fluid path, said damper means being mechanically coupled to said pump means;
   (d) a bypass valve means for directing said first and second fluids to said fluid jet means and to a heat exchanger means, said valve means being mechanically coupled to said pulsation damper means;
   (e) a heat exchanger means for maintaining said first and second fluids at a suitable temperature for human contact, said heat exchanger means being mechanically coupled at an input end to said bypass valve and at an output end to an input end of said pump means;
   (f) a circulating return line for coupling to said bypass valve and forming a closed loop during said initial sterile preparation; and
   (g) an injection port for injecting secondary fluids and substances as needed.

14. An aseptic system apparatus for use in medical, microelectronic and aerospace industries as recited in claim 13, wherein said pump means being a positive displacement pump that provides pressures in the range of 300-1000 psi, said pump being modified to have seals, O-rings, and cups made from a highly chemical resistive material, such as VITON and TEFLON and adapted to provided said injection port.

15. An aseptic system apparatus for use in medical, microelectronic and aerospace industries as recited in claim 7, wherein said enclosure means further comprises:
   (a) at least one pair of glove ports for allowing access said enclosure means for enabling a technician to engage said fluid jet means and to manipulate said article for cleaning within said enclosure means;
   (b) a transparent lid provided on a top portion of said enclosure means for allowing viewing of said article that is being cleaned;
   (c) at least one storage vesicle located on a wall of said enclosure means for storing articles such as those that have been cleaned; and
   (d) a drain port located on a bottom surface of said enclosure means, said drain port being covered by said wall and floor liner means.

16. An aseptic system apparatus for use in medical, microelectronic and aerospace industries as recited in claim 15, wherein said enclosure means further comprises:
   (a) an enclosure body member, said enclosure body member being manufactured from a polycarbonate, vacuumed molded material, said enclosure body member being a disposable item; and
   (b) said enclosure body member being provided with coupling means for being mechanically coupled to said sterile fluid path.

17. An aseptic system apparatus for use in medical, microelectronic and aerospace industries, said aseptic system apparatus comprising:
   at least one stage cleaning station for cleaning of particulates from an article used in said industries, said at least one stage cleaning station comprising a sterile ultrasonic bath apparatus member, said sterile ultrasonic bath apparatus member comprises,
   (i) at least one ultrasonic cleaning tank for submersing and ultrasonically cleaning said article,
   (ii) a first liquid contained in said tank for use during an initial sterile preparation of said ultrasonic bath apparatus member,
   (iii) a second liquid contained in said tank after said initial sterile preparation for use during ultrasonic cleaning,
   (iv) a transducer means for generating ultrasonic energy within said second liquid for facilitating said ultrasonic cleaning, said transducer means having an operating frequency that enables excition of said second liquid to cavitation without significantly eroding said article being cleaned,
   (v) a heat exchanger means for maintaining said second liquid and said article at a specified working temperature range by removing thermal energy in said second liquid, said heat exchanger means being hydraulically coupled to said at least one ultrasonic cleaning tank, and
   (vi) a variable flow rate peristaltic pump, said pump being hydraulically coupled to said heat exchanger means and to said at least one ultrasonic cleaning tank to form a closed hydraulic loop system, said pump being provided with a control circuit for cycling said bath fluid at a variable flow rate to maintain said second liquid within said specified working temperature range.

* * * * *